United States Patent [19]
Davis et al.

[11] Patent Number: 5,353,811
[45] Date of Patent: Oct. 11, 1994

[54] TRAP

[76] Inventors: Sandra L. Davis, 3325 Cherokee Ave., San Diego, Calif. 92104-4412; Michael G. Kielty, 3023 Bunker Hill St., Ste. 201 San Diego, Calif. 92109

[21] Appl. No.: 845,400

[22] Filed: Mar. 4, 1992

[51] Int. Cl.[5] .............................................. A61F 5/37
[52] U.S. Cl. ..................................... 128/883; 128/884
[58] Field of Search ......... 128/884, 883, 830, 831–840

[56] References Cited

U.S. PATENT DOCUMENTS

| | | | |
|---|---|---|---|
| 14,739 | 4/1856 | Sibley | 128/883 |
| 826,377 | 7/1906 | Sonn | 128/883 |
| 934,240 | 9/1909 | Tunnessen | 128/883 |

FOREIGN PATENT DOCUMENTS 2844840  4/1980  Fed. Rep. of Germany ...... 128/884

*Primary Examiner*—Michael A. Brown

[57] ABSTRACT

The invention is made of a flexible metal rim(6) containing within its circumference plastic, triangular, pointed, curved spears(2), which move only inward. Attached to the rim(6) is a thin, hollow, rubber pocket (3), reinforced in a cage-like manner with heavier rubber(4). It can be pre-lubricated in the manner of a condom. It is inserted into the vagina by the woman wearing it by folding the pocket(3) lengthwise and pushing it into the vaginal cavity. Upon release, the pocket(3) expands slightly to fill the vaginal cavity. The flexible metal rim(6) can then be pushed upward to fit into the outer end of the vaginal opening (8). It has two small lips(1), at the top and bottom of the flexible rim(6), which are used as grips for removal. A woman can pry either lip(1) with a thumbnail or fingernail and draw the invention out of the vagina. It is disposable. It can be worn for a few hours or all night. Possibly it should not be worn for more than 24 hours, as an association between wearing it and toxic shock syndrome in some women will not have been established. A physician can be consulted as to proper insertion and care. It can be made in small, medium and large sizes to accommodate different vaginas and it can be worn by women of all ages. It can be made of several types of rubber and plastic, some more flexible than others.

1 Claim, 2 Drawing Sheets

TRAP

BRIEF SUMMARY

The nature of the invention is one of bodily harm to men during the act of rape. It is an intra-vaginal anti-rape device which consists of a thin rubber pocket, reinforced in a cage-like manner with heavier rubber, which fills the vaginal cavity and has at its open end, at the vaginal opening, a flexible metal rim containing, within its circumference, pointed, curved, plastic spears which trap a rapist's penis by embedding their points under the head of the penis upon outward movement. The object of the invention is to cause enough bodily harm to a rapist as to necessitate emergency medical treatment, possibly surgical treatment, and to prevent the spread of sexually transmitted diseases, such as Aids, and unwanted pregnancies due to rape.

Men contemplating rape, after the use of this invention becomes known, might not attempt it for fear that any woman might be wearing this invention.

DETAILED DESCRIPTION

Figure 1:
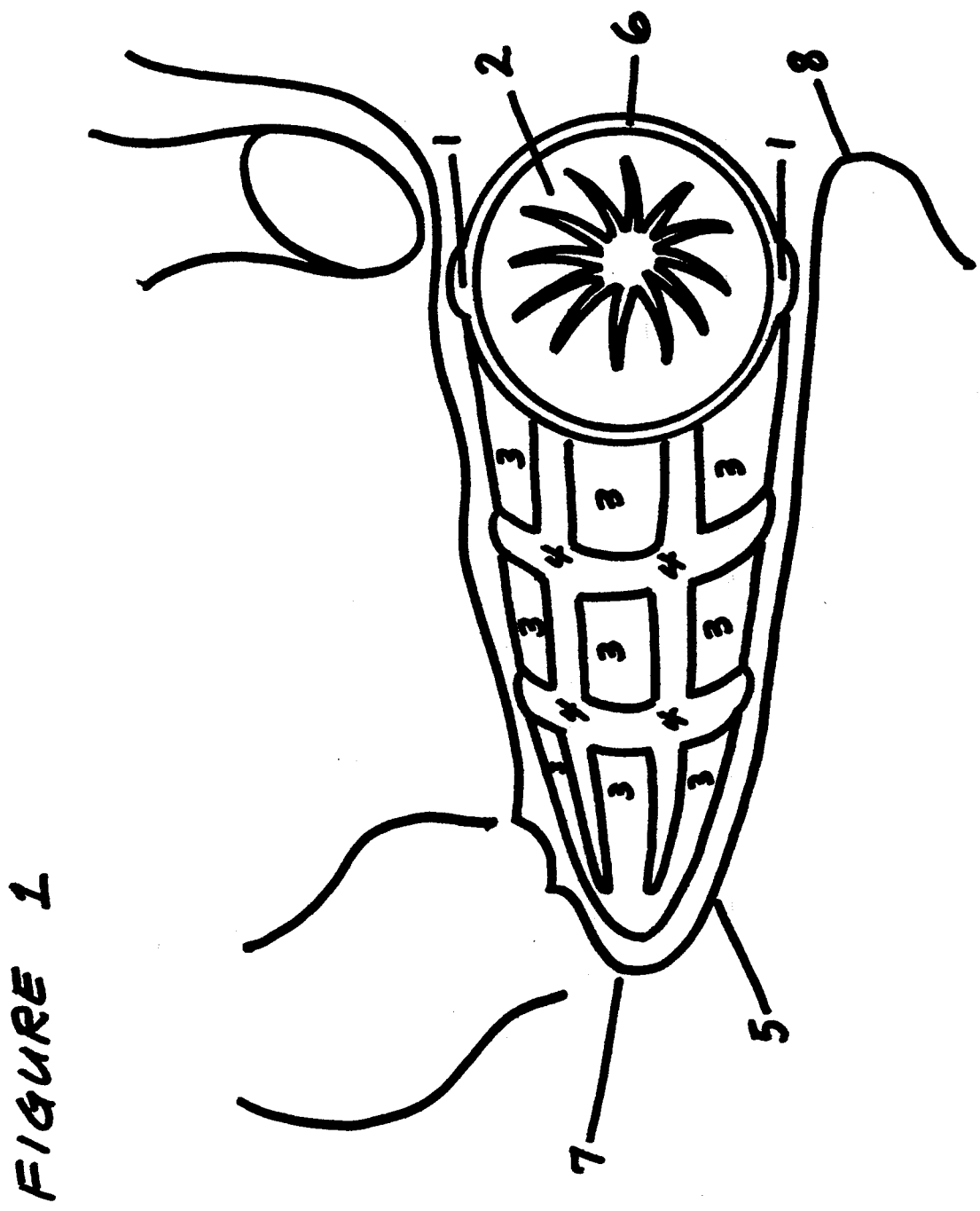
FIG. 1 shows the invention from the outer side. The end consists of a flexible metal rim(6) with triangular, pointed, curved, plastic spears(2) and a hollow elongated pocket of thin rubber(3) reinforced in a cage-like manner with heavier rubber(4). The invention fills the vagina(5), the closed end of the pocket being at the inner end of the vagina(7) and the open end of the pocket being at the outer end of the vagina(8). It would trap any fluid ejaculated from the penis of a rapist during sexual intercourse. The points of the spears(2) would embed themselves under the head of the penis during outward movement causing great pain, bleeding and possibly death.
Figure 2:
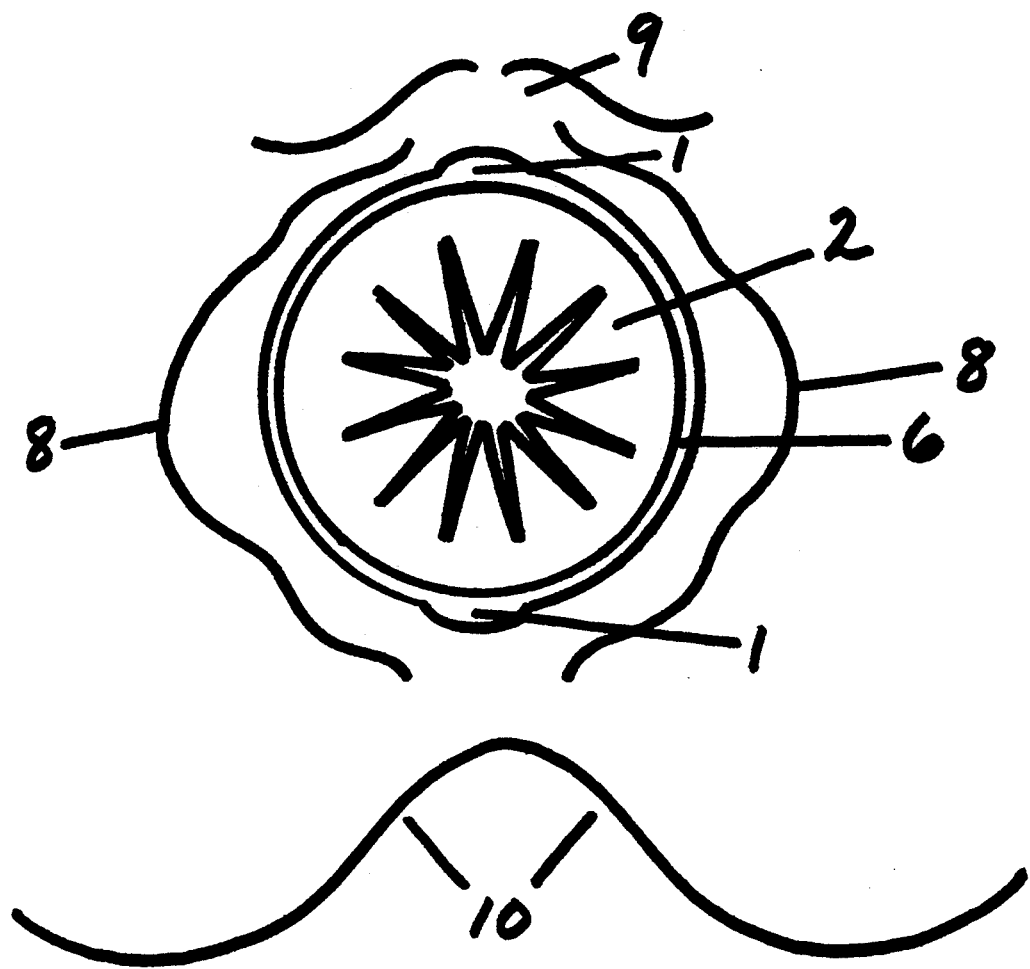
FIG. 2 shows the open-end view or vaginal entrance view of the invention. It has a flexible, metal rim(6) with two small lips(1), used as grips for removal by the woman wearing it, one near the front(9) and one near the rear(10) of the body, and has triangular, pointed curved, plastic spears(2) within the circumference of the rim(6) which only move inward. The penis of a rapist is inserted into the vagina through the opening of this invention and upon outward movement the points of the spears(2) embed themselves under the head of the penis, causing great pain, bleeding and even death.

The subject matter which we regard as the invention is an elongated pocket of thin rubber(3) reinforced with heavier rubber(4) in a cage-like manner, and fits into a woman's vagina(5), the closed end of the pocket being at the inner end of the vagina(7) and the open end of the pocket being at the outer end of the vagina(8), and that open end consisting of a circular, reinforced, flexible metal rim(6) containing within its circumference pointed, curved, plastic spears(2) which point only inward into the empty cavity of the pocket. The flexible metal rim has two lips(1), one at the upper edge and one at the lower edge of the opening of the invention. These lips(1) project slightly outward from the rim(6) and provide grips for the removal of the invention by the woman wearing it. The thumbnail or other fingernail can pry the lip(1) outward at an angle and the pocket can be drawn out of the vagina(5). The invention inserted into a woman's vagina is a weapon against the act of rape. When a woman is raped the penis of the rapist enters the vagina through the invention and is enclosed in the pocket of the invention. When the penis is pulled out the spears(2) catch it by embedding their points under the head of the penis and the spears out into the flesh, causing great pain, bleeding, a need for emergency medical treatment and possibly death. The invention described herein could be so embedded under the head of the penis that it would be pulled out of the vagina, attached to the penis, when the rapist senses pain, and it could necessitate surgical removal. The invention inserted into a woman's vagina protects her from unwanted semen, as any fluid ejaculated through a penis into the pocket of the invention would be contained therein. This would protect her from an unwanted pregnancy as a result of being raped and could protect her from the spread of Aids and other sexually transmitted diseases from a rapist who had such a disease. This could protect women from being raped by acting as a deterrent, because once this invention became known to the public, a rapist might be fearful of any woman wearing it. Rape is an act of violence and this invention is an equal and passive answer to that act.

This invention could be made in three sizes, small, medium and large, to accommodate different vaginal sizes. It could also be made in several types, some more flexible than others. It would be disposable. Continuous wearing of the invention for more than 24 hours would probable not be recommended as there might be an association between wearing the invention and toxic shock syndrome in some women. A physician could be consulted as to proper placement in the vagina as well as proper instructions as to its placement in the package in which it is sold. It should carry a disclaimer in case a woman inserts it incorrectly. It should carry a warning that it might cause other violent acts against her person. It should carry a warning that it causes bodily harm and possibly death to a man during sexual intercourse.

The knowledge that women could be wearing this device could eventually deter the act of rape. We cannot assume that violence against women would stop. However, this invention could shield women where they are otherwise very vulnerable and defenseless.

We claim:

1. An intra-vaginal anti-rape device comprising an elongated pocket having a longitudinal axis, said pocket is made of a thin rubber, and reinforced along its longitudinal axis with a cage-shaped thicker rubber;

a circular, metal rim attached to an open end of said pocket, said rim having sharp, curved, plastic spears attached within its circumference;

a lip including two flat extensions that extend outwardly from opposite sides of said rim, wherein said device can be removed from the vagina through prying the lip away from the mouth the vagina, wherein said device is adapted to act as a trap during rape.

* * * * *